US00PP12573P2

(12) United States Plant Patent
Cherry

(10) Patent No.: US PP12,573 P2
(45) Date of Patent: Apr. 23, 2002

(54) LAVENDER PLANT NAMED 'BEE HAPPY'

(76) Inventor: Robert J. Cherry, RMB 2117 Greta Road, Kulnura, 2250, New South Wales (AU)

( * ) Notice: Subject to any disclaimer, the term of this patent is extended or adjusted under 35 U.S.C. 154(b) by 0 days.

(21) Appl. No.: 09/728,899

(22) Filed: Dec. 4, 2000

(51) Int. Cl.[7] ..... A01H 5/00

(52) U.S. Cl. ..... Plt./226

(58) Field of Search ..... Plt./226

(56) References Cited

PUBLICATIONS

UPOV–ROM GTITM Computer Database, 2001/03 GTI Jouve Retrieval Software, citation for 'Bee Happy'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Lavender plant named 'Bee Happy', characterized by its upright plant habit; dense and bushy plant form; vigorous growth habit; gray green-colored leaves; and purple-colored flower corollas with showy white-colored terminal flower bracts.

2 Drawing Sheets

BACKGROUND OF THE INVENTION

The present Invention relates to a new and distinct cultivar of Lavender plant, botanically known as *Lavandula stoechas L.*, and hereinafter referred to by the name 'Bee Happy'.

The new Lavender is a product of a planned breeding program conducted by the Inventor in Kulnura, New South Wales, Australia. The new Lavender originated from a cross made by the Inventor of two unnamed proprietary selections of *Lavandula stoechas L.*, not patented. The new Lavender was selected by the Inventor in 1998 on the basis of its compact and freely flowering habit. Plants of the new Lavender are more compact and more freely flowering than plants of the parental selections.

Asexual reproduction of the new cultivar by terminal cuttings taken at Kulnura, New South Wales, Australia, has shown that the unique features of this new Lavender are stable and reproduced true to type in successive generations.

SUMMARY OF THE INVENTION

Plants of the cultivar Bee Happy have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Bee Happy'. These characteristics in combination distinguish 'Bee Happy' as a new and distinct cultivar:

1. Upright plant habit.
2. Dense and bushy plant form.
3. Vigorous growth habit.
4. Gray green-colored leaves.
1. Purple-colored flower corollas with showy white-colored terminal flower bracts.

Plants of the cultivar Bee Happy can be compared to plants of the *Lavandula stoechas L.* cultivar Marshwood. However in side-by-side comparisons conducted by the Inventor in Kulnura, New South Wales, Australia, plants of the cultivar Bee Happy and the cultivar Marshwood differ in the following characteristics:

1. Plants of the new Lavender have shorter leaves than plants of the cultivar Marshwood.
2. Plants of the new Lavender have gray green-colored leaves whereas plants of the cultivar Marshwood have green-colored leaves.
3. Plants of the new Lavender have smaller terminal flower bracts than plants of the cultivar Marshwood.
4. Plants of the new Lavender have white-colored terminal flower bracts whereas plants of the cultivar Marshwood have light lavender-colored terminal bracts.
5. Plants of the new Lavender have shorter and stronger peduncles than plants of the cultivar Marshwood.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Lavender.

The photograph on the first sheet comprises a side perspective view of a typical flowering plant of 'Bee Happy' grown in a container.

The photograph on the second sheet comprises a close-up view of typical flowering spikes of 'Bee Happy'.

DETAILED BOTANICAL DESCRIPTION

In the following description, color references are made to The Royal Horticultural Society Colour Chart where general terms of ordinary dictionary significance are used. Plants were grown under greenhouse conditions which closely approximate commercial production conditions during the spring in Kulnura, New South Wales, Australia. Plants used for this description were grown for about 16 to 24 weeks after planting in 15-cm containers.

Botanical classification: *Lavandula stoechas L.* cultivar Bee Happy.

Parentage:

*Female parent*.—Unnamed proprietary selection of *Lavandula stoechas L.*, not patented.

*Male parent*.—Unnamed proprietary selection of *Lavandula stoechas L.*, not patented.

Propagation:

*Type cutting*.—Terminal vegetative cuttings.

*Time to initiate roots*.—About 10 to 14 days at 18 to 21° C.

*Root description*.—Fine, well-branched.

Plant description:

*Form*.—Perennial plant with upright plant habit. Flowers in verticillasters in crowded spikes with large showy terminal bracts. Freely branching with lateral branches forming at every node; dense and bushy.

*Crop time*.—From planting, about 16 to 24 weeks are required to produce finished flowering plants in 15-cm containers.

*Plant height* (*soil level to top of plant plane*).—About 50 cm.

*Vigor*.—Vigorous growth habit.

*Foliage description*.—Leaves simple, opposite, decurrent. Length: About 4.1 cm. Width: About 6 mm. Shape: Linear. Apex: Mucronate. Base: Cuneate. Margin: Entire; edges recurved. Texture: Fine pubescence on upper surface; lower surface, smooth. Fragrance: Very aromatic. Color: Young foliage, upper and lower surfaces: 138B. Mature foliage, upper and lower surfaces: 189A, venation, 189A.

Flower description:

*Flower arrangement and shape*.—Small single flowers in verticillasters in crowded spikes; about 7 to 8 rows of flowers; flowers with small bracts and large showy terminal bracts; calyx ovoid-tubular; corolla tube longer than calyx, 2-lipped.

*Natural flowering season*.—Continuous throughout the Spring.

*Flower longevity on the plant*.—Longevity of individual flowers is highly dependent on weather conditions. Flowers not persistent, terminal flower bracts persistent.

*Inflorescence size*.—Length (excluding terminal flower bracts): About 3.6 cm. Diameter: About 1 cm.

*Flowers*.—Length: About 4 mm. Diameter: About 2 mm. Corolla color: Upper and lower surfaces, 93C.

*Terminal flower bracts*.—Arrangement: About four in a single whorl. Length: About 1.73 cm. Width: About 8.5 mm. Shape: Obovate. Apex: Obtuse. Base: Attenuate. Margin: Entire. Texture: Smooth. Color: Both surfaces, 155A with green venation.

*Peduncle*.—Strength: Moderately strong. Length: About 8.1 cm. Diameter: About 2 mm. Color: Close to 145B.

*Seed*.—Length: About 2 mm. Diameter: About 2 mm. Color: 199A.

Disease resistance: Plants of the new Lavender have not been noted to be resistant to pathogens common to Lavender.

Weather tolerance: Plants of the new Lavender have exhibited good tolerance to rain and wind.

It is claimed:

1. A new and distinct cultivar of Lavender plant named 'Bee Happy', as illustrated and described.

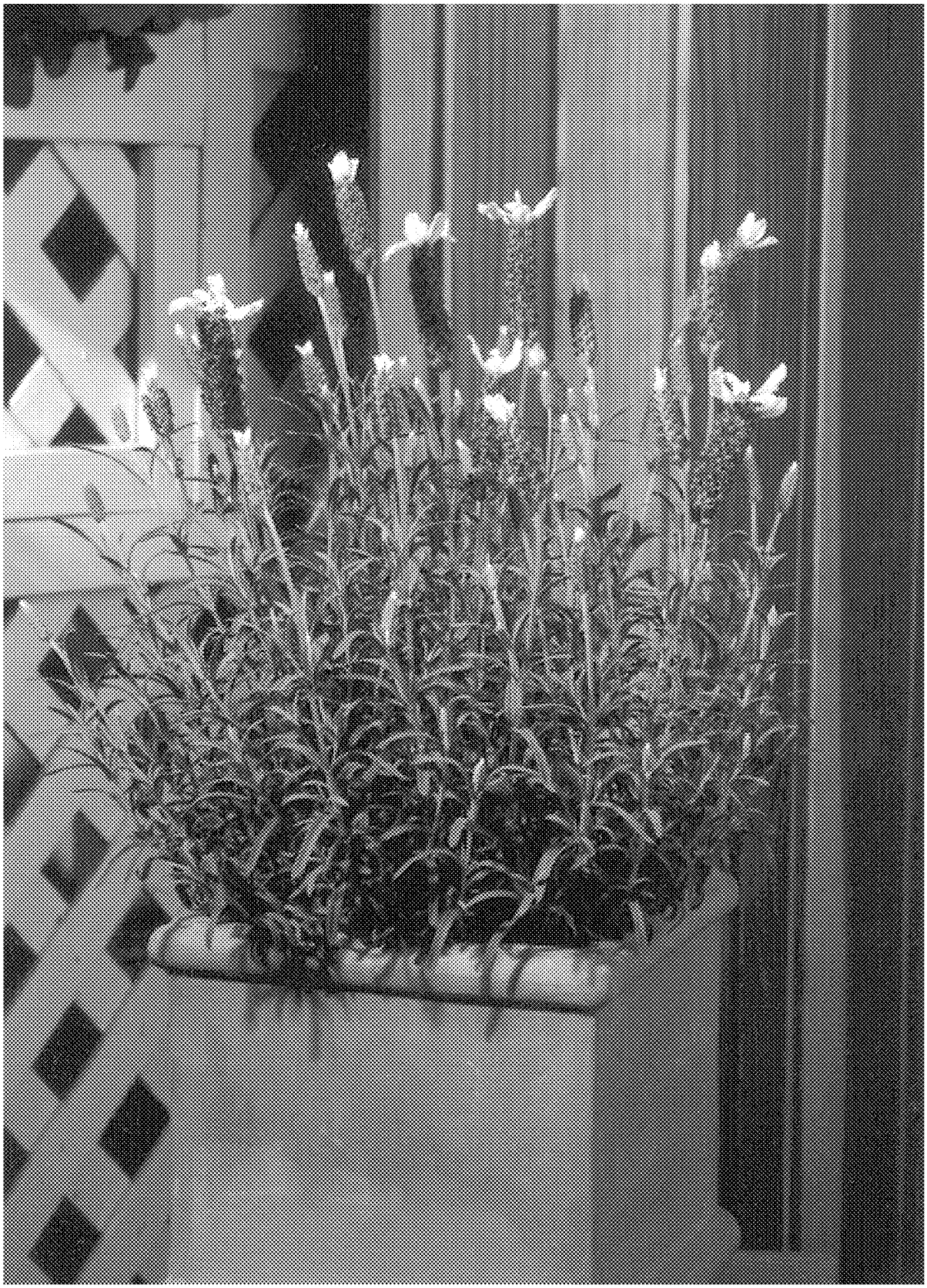

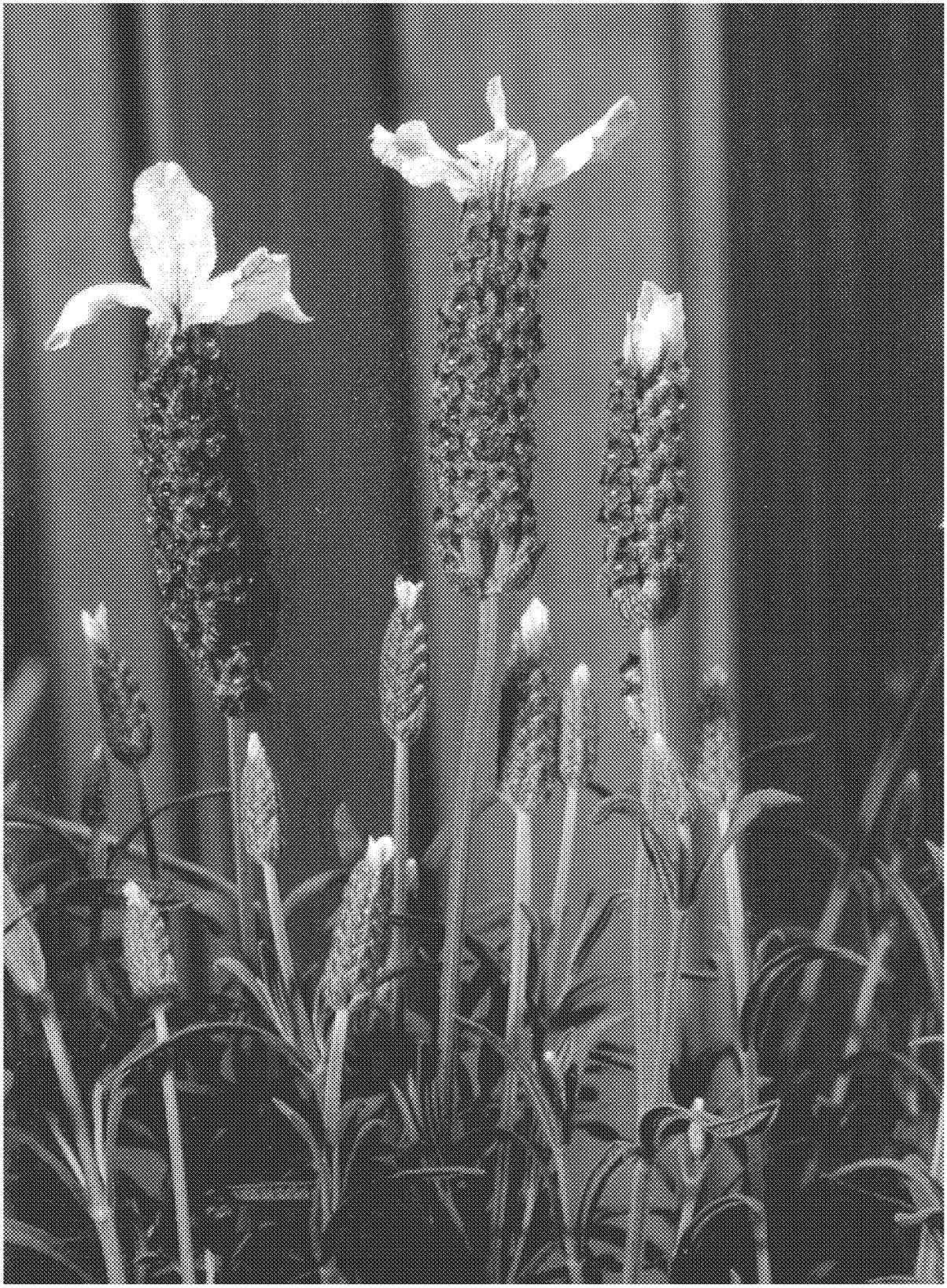

* * * * *